United States Patent
Harris, Jr. et al.

(10) Patent No.: US 7,264,623 B2
(45) Date of Patent: Sep. 4, 2007

(54) TISSUE GRASPING INSTRUMENT AND METHOD FOR USE IN ARTHROSCOPIC SURGERY

(75) Inventors: Brian R. Harris, Jr., Cordova, TN (US); Stephen J. Snyder, Encino, CA (US)

(73) Assignee: Wright Medical Technology, Inc., Arlington, TN (US)

( * ) Notice: Subject to any disclaimer, the term of this patent is extended or adjusted under 35 U.S.C. 154(b) by 587 days.

(21) Appl. No.: 10/687,152

(22) Filed: Oct. 16, 2003

(65) Prior Publication Data

US 2005/0085850 A1 Apr. 21, 2005

(51) Int. Cl.
*A61B 17/04* (2006.01)

(52) U.S. Cl. .................... 606/148; 606/207

(58) Field of Classification Search ........ 606/205–211, 606/148; D8/4, 52; D24/143
See application file for complete search history.

(56) References Cited

U.S. PATENT DOCUMENTS

| | | | | |
|---|---|---|---|---|
| 755,440 | A * | 3/1904 | Bonschur | 81/3.6 |
| 2,504,202 | A * | 4/1950 | Kadavy | 606/147 |
| 4,803,983 | A * | 2/1989 | Siegel | 606/151 |
| 5,222,962 | A * | 6/1993 | Burkhart | 606/148 |
| 5,257,637 | A * | 11/1993 | El Gazayerli | 128/898 |
| 5,382,258 | A * | 1/1995 | Chow | 606/148 |
| 5,562,699 | A * | 10/1996 | Heimberger et al. | 606/205 |
| 5,776,150 | A * | 7/1998 | Nolan et al. | 606/148 |
| 5,919,206 | A * | 7/1999 | Gengler et al. | 606/205 |
| 6,228,104 | B1 * | 5/2001 | Fogarty et al. | 606/207 |
| 6,273,887 | B1 * | 8/2001 | Yamauchi et al. | 606/48 |
| 6,309,404 | B1 * | 10/2001 | Krzyzanowski | 606/208 |
| 6,839,949 | B1 * | 1/2005 | Miknich | 29/402.19 |
| 2002/0103493 | A1* | 8/2002 | Thal | 606/144 |

FOREIGN PATENT DOCUMENTS

GB 2210574 A * 6/1989

* cited by examiner

*Primary Examiner*—Anhtuan T. Nguyen
*Assistant Examiner*—Elizabeth Houston

(57) ABSTRACT

A tissue grasping instrument and method for use in arthroscopic surgery is disclosed. Typically, the instrument will be used in the manipulation of sutures and a graft in the form of an acellular matrix during the repair of rotator cuffs.

14 Claims, 6 Drawing Sheets

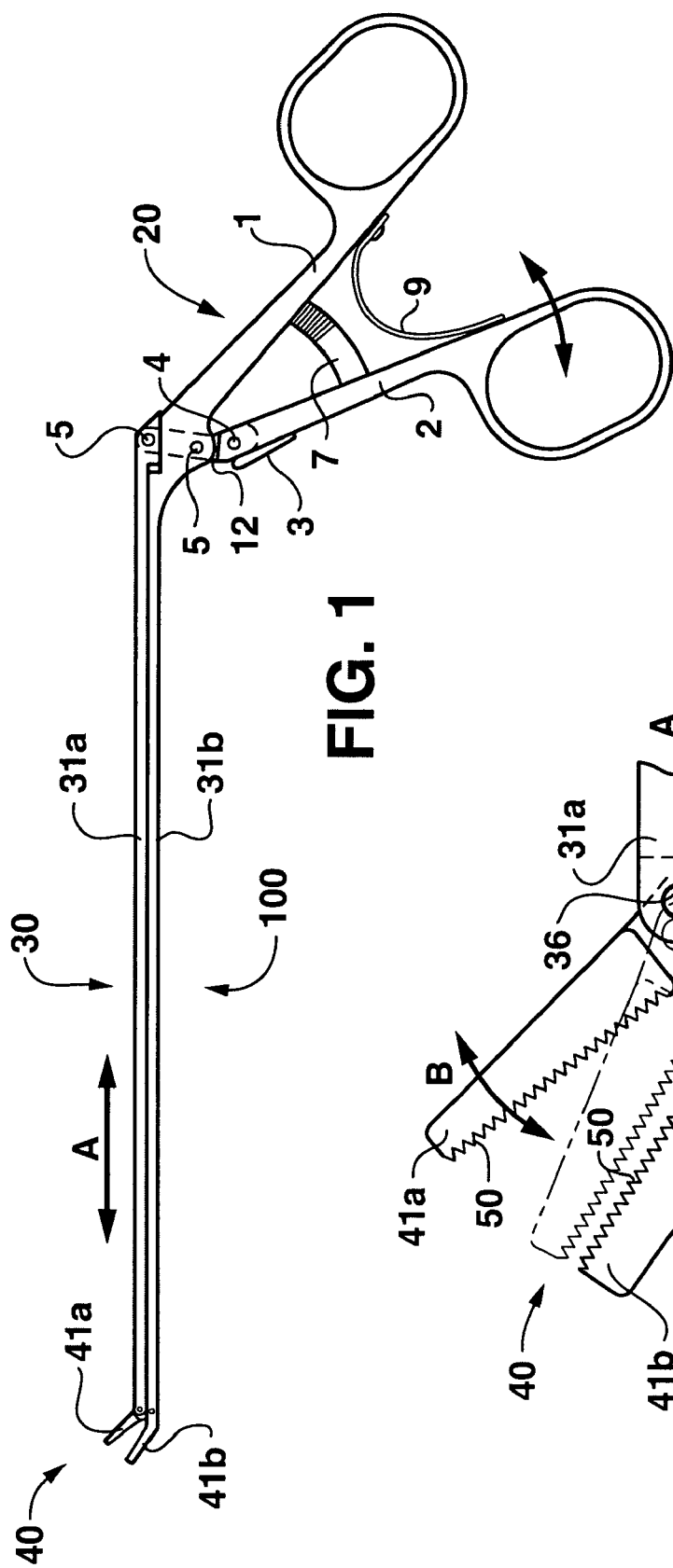
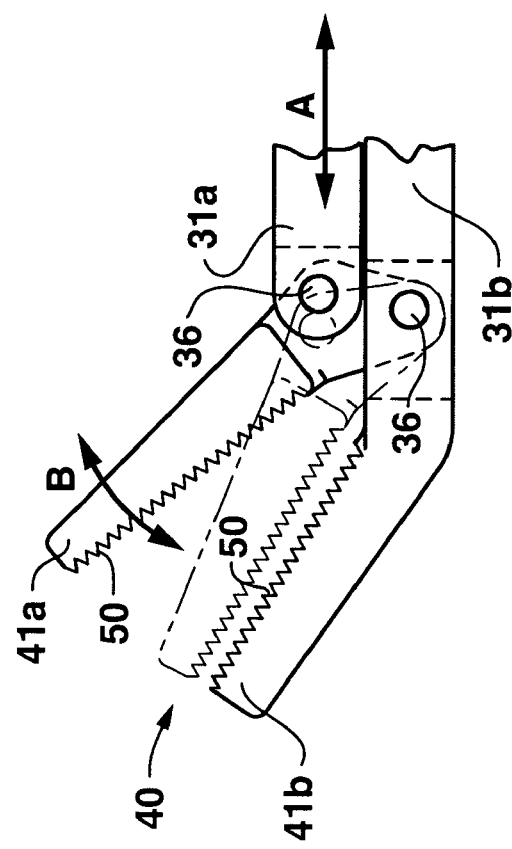

TISSUE GRASPING INSTRUMENT AND METHOD FOR USE IN ARTHROSCOPIC SURGERY

FIELD OF THE INVENTION

This invention generally concerns instrumentation and methods useful in the field of arthroscopic surgery. The invention specifically concerns instrumentation and methods useful in handling and stitching tissues and tissue grafts during arthroscopic rotator cuff repair surgery.

BACKGROUND OF THE INVENTION

In the field of arthroscopic surgery, typically proper instrumentation can is important to a successful procedure. Accordingly, a large number of specialized instruments have been developed, some with very fine differences from existing instruments, mainly to meet specific needs or doctor preferences. For example, some instruments, such as U.S. Pat. No. 5,947,982, incorporated entirely herein by reference, only pass sutures and do not grasp tissue. In general, the needs of arthroscopic or "closed" surgery are discussed in U.S. Pat. No. 5,843,100, whose contents are also entirely incorporated herein by reference.

U.S. Pat. No. 5,575,801, issued Nov. 19, 1996 and incorporated entirely herein by reference, shows a method and apparatus for use in arthroscopic rotator cuff surgery. In this patent, a trigger operated tool is shown for grasping the rotator cuff and holding it over the shoulder bone. The upper jaw of the instrument has an aperture and the lower jaw has a slot. The aperture and slot are aligned when the jaw is closed. As shown in FIG. 3B of that patent, the hole in the first jaw is used to remove the suture from the body while the jaw is closed. The method and instrument of this patent combine to form an older more traditional regimen for fixing torn rotator cuffs because grafts are not used.

However, in more advanced and modern rotator cuff procedures, a graft of some type is used to fill the gap formed by the torn area or the poor tissue quality of the rotator cuff, either of which may be incapable of handling anchoring forces on their own. In such procedures,this graft: (1) needs to be sutured before and after placement in the body, (2) the sutures need to be manipulated in situ as the graft is sutured to the rotator cuff and anchored to the bone, and (3) then the excess suture threads need to be removed after implantation of the graft in the patient. An exemplary graft material is GRAFTJACKET™ acellular matrix, sold by Wright Medical Technology, Inc., of Arlington, Tenn. , the assignee of this application. The acellular matrix is manufactured according to U.S. Pat. Nos. 4,865,871; 5,024,830; and 5,336,616.

Accordingly, a specialized tool and method capable of being used for this purpose and through an arthroscopic (e.g. 7 mm) cannula is needed.

Therefore, there is room for improvement in the art.

SUMMARY OF THE INVENTION

It is an object of the invention to provide a surgical instrument, comprising: a handle portion; a body portion; a jaw portion, the jaw portion comprising first and second jaws for gripping tissue there between; wherein the second jaw has a closed perimeter hole extending there through.

It is a further object of the invention to provide an arthroscopy method, comprising the steps of: grasping a tissue between first and second jaws of an instrument, one of the jaws having a center hole and the other of the jaws having a u-shaped opening; passing a suture through the tissue and the center hole of the one jaw and the u-shaped opening of the other jaw; opening the jaws to release the tissue from the grasp of the jaws and release the suture from the jaw with said u-shaped opening; and pulling the thread with the instrument while the jaws are opened.

It is yet a further object of the invention to provide a method of using a surgical instrument having a first jaw having a slit and a second jaw having a hole, comprising the steps of: grasping a portion of a tissue between the first and second jaws; puncturing the tissue with a hollow surgical needle in the area of the slit of the first jaw and the hole of the second jaw.

These and other objects of the invention are described herein.

BRIEF DESCRIPTION OF THE DRAWINGS

FIG. 1 depicts an exemplary embodiment of a tissue grasping instrument according to the invention.

FIG. 2A depicts a plan view of an exemplary embodiment of the jaw portion of a tissue grasping instrument according to the invention.

DETAILED DESCRIPTION OF THE INVENTION

Figure 2B:
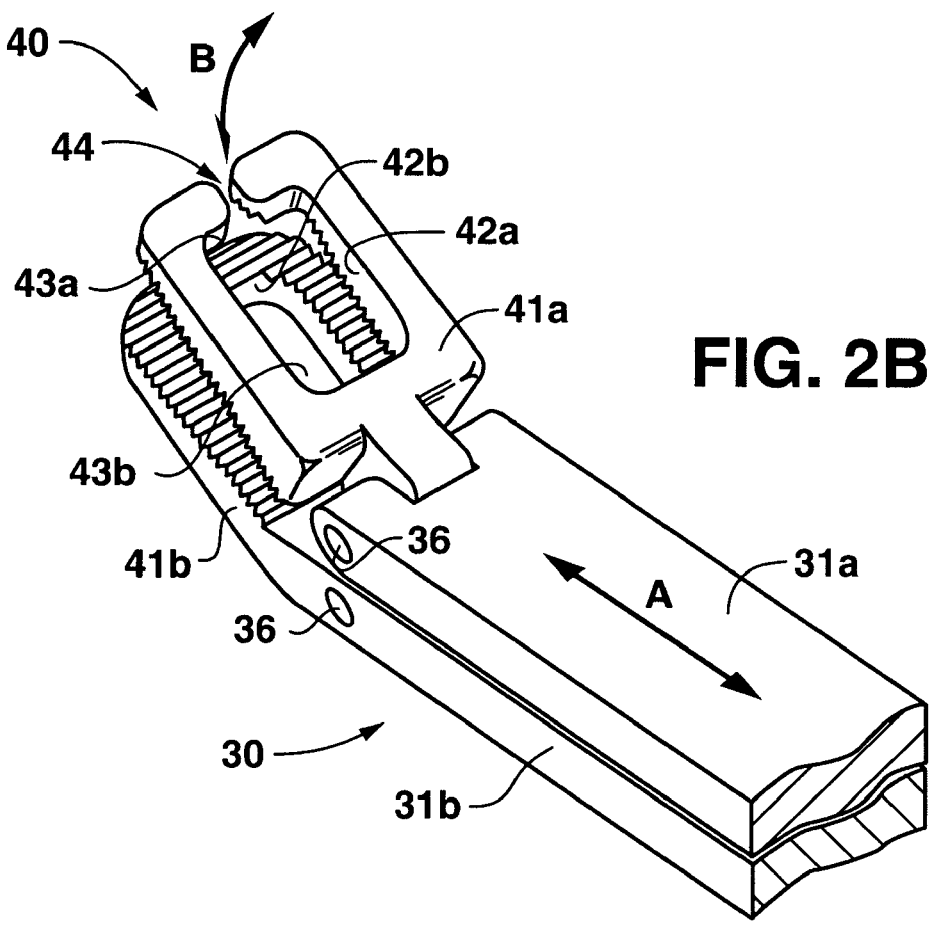
FIG. 2B depicts a perspective view of an exemplary embodiment of the jaw portion of a tissue grasping instrument according to the invention.

FIG. 1 depicts an exemplary embodiment of a tissue grasping instrument 100 according to the invention.

Tissue grasping instrument 100 generally comprises a handle portion 20, a body portion 30, and a jaw portion 40.

Jaw portion 40 comprises first and second jaws 41a, 41b. As shown by arrow B in FIGS. 2A and 2B, first and second jaws 41a, 41b are designed to move with respect to each other, preferably, but not absolutely, as described as follows. Second jaw 41b is at least integral, and preferably unitary (for ease of construction) with second elongated body portion 31b. First jaw 41a is pivotally mounted to both of the first and second elongated body portions 31a, 31b, by any suitable mechanism, preferably pivot pins 36 as shown. Accordingly, as the elongated body portions 31a, 31b linearly move with respect to each other, e.g., first elongated body member 31a moves in the direction of arrow A, the first jaw 41a is caused to pivot in the direction of arrow B. This mechanism or mechanisms closely similar thereto are well known in this field of art and shown, for example, in U.S. Pat. Nos. 5,318,579 and 5,961,530, both of whose contents are incorporated by reference herein. Both jaws 41a, 41b have a plurality of teeth 50, whose details will be discussed below.

During use of tissue grasping instrument 100, the instrument will be positioned such that first and second jaws 41a, 41b will typically be the upper and lower jaws, respectively.

Figure 2C:
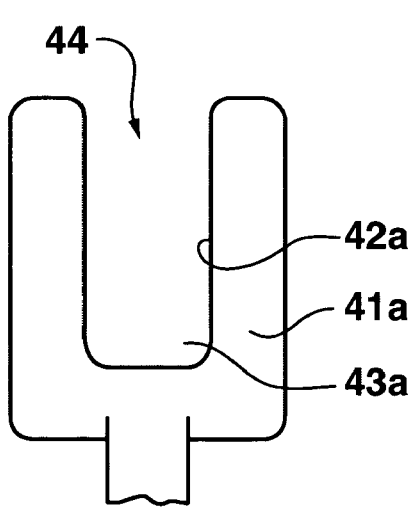
FIG. 2C depicts a plan view of a first alternative embodiment of a first jaw for use with a tissue grasping instrument according to the invention.
Figure 2D:
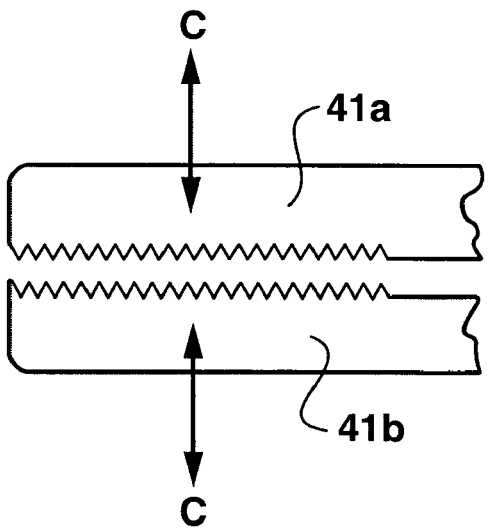
FIG. 2D depicts an elevation view of a second alternative embodiment of a jaw for use with a tissue grasping instrument according to the invention.

Optionally, as shown in FIG. 2D, through the use of connecting arms and linkages (not shown), the jaws 41a, 41b, may open and close via pure vertical movement (arrows C) rather than pivoting, whereby jaws 41a, 41b are always parallel with each other. The use of parallel closing jaws 41a, 41b allow for the even distribution of clamping force across a larger surface area for a wide range of tissue thicknesses.

Handle portion 20 comprises first and second finger grip bodies 1, 2. First finger grip body 1 is typically unitary with second elongated body 31b, but can be integral therewith. Second finger grip body 2 is linked to first elongated body 31a through pivot arm 12 and pins 5. Pivot arm 12 may either be unitary with finger grip 2 and first elongated body member 31a or a separate member linked by pivot pins (not shown). Thus, as first and second finger grip bodies 1, 2 are moved towards and away from each other, this causes relative linear movement between first and second elongated bodies 31a, 31b, as known in the art from the patents listed above and incorporated by reference herein.

Optional ratchet arm 7 has two purposes. First, ratchet arm 7 can be used to make sure when second finger grip body is moved towards first finger grip body, it does so in the proper plane and there is no twisting of tissue grasping instrument 100 that could cause tissue grasping instrument 100 to fail. Second, ratchet 7 capable of locking the tissue grasping instrument 100 and hence jaw portion 40 at specific incremental positions. Such use is described, for example, in U.S. Pat. No. 5,613,977 whose contents are incorporated by reference herein.

Spring 9 can be used to provide feedback to the user. Finger grip body 2 has an additional pivot linkage point 4 with pivot arm 12. Planar spring 3 normally causes finger grip 2 to move with pivot arm 12. However, if too much force is applied to finger grip body 2 (i.e., would damage tissue in jaw 40), spring 3 gives way, causing finger grip body 2 to move with respect to pivot arm 12. Therefore, spring 3 acts as a safety bias against application of an over pressure to the tissue or graft as second finger grip body 2 is moved towards first finger grip body 1.

All major component parts of tissue grasping instrument 100 are typically made of stainless steel; however, it is possible to make tissue grasping instrument 100 out of plastic for one-time use unless the overall structure of tissue grasping instrument 100 becomes too complex, such as with the addition of the optional ratchet arm 7 and spring 3 and 9.

FIG. 2B depicts a perspective view of an exemplary embodiment of the jaw portion of a tissue grasping instrument 100 according to the invention. First jaw 41a has a center hole 43a bound by a perimeter wall 42a that has a narrower slit/slot 44 in communication therewith, typically in the free end of first jaw 41a opposite the body portion 30. Second jaw 41b just has a closed center hole 43a bound by perimeter wall 42b. The center holes 43a, 43b will typically be coaxial and the same size, though neither of these are necessary or critical. Both center holes 43a, 43b go completely through their respective jaw members 41a, 41b.

As shown in FIG. 2C, it is possible for slit 44 to be so wide that first jaw 41a can be considered u-shaped and having an open center portion 43a.

Figure 3:
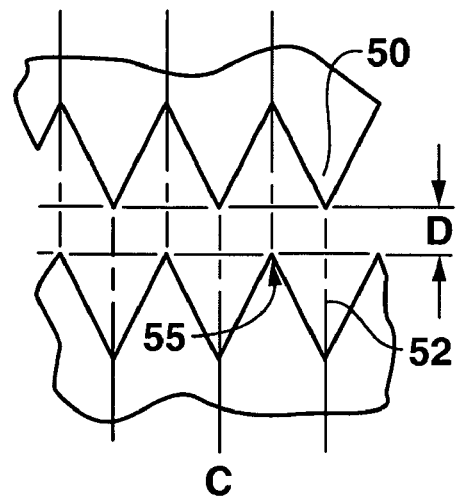
FIG. 3 depicts a close up of the teeth structure of an exemplary embodiment of the jaw of a tissue grasping instrument according to the invention.

FIG. 3 depicts a close up of the teeth 50 structure of an exemplary embodiment of the jaw portion 40 of a tissue grasping instrument 100 according to the invention. As previously mentioned, each of first and second jaws 41a, 41b have a plurality of teeth 50. Each tooth 50 is spaced from the adjacent tooth 50 by a trough 52, whose shape and/or form is immaterial. While teeth 50 are shown herein as having pointed tips 52, other tip configurations are possible if they allow for grasping tissue. Tips 51 may be coated with materials 55 for protecting the grasped material. Such coating materials are typically soft materials (relative to the material of the teeth 50) and may include silicon-based coatings. The teeth 50 of first jaw 41a are preferably out of phase with the teeth 50 of second jaw 41b and line up with troughs 52 of second jaw 41b as shown by phantom lines C. Similarly, the teeth 50 of second jaw 41b are preferably out of phase with the teeth 50 of first jaw 41a and line up with troughs 52 of first jaw 41a as also shown by phantom lines C. Furthermore, when jaw portion 40 is closed, the tips 51 of teeth 50 do not come into contact with each or fill each others' troughs 52; they are spaced apart by a predetermined distance D. This is because tissue grasping instrument 100 is intended for use with a particular acellular matrix that should not be subjected to undue squeezing, etc., and is not intended merely for grasping suture thread or tissue resistant to squeezing as in the prior art such as U.S. Pat. Nos. 5,797,927 and 6,554,844 and U.S. Published Application No. 2003/0083695.

Figure 4A:
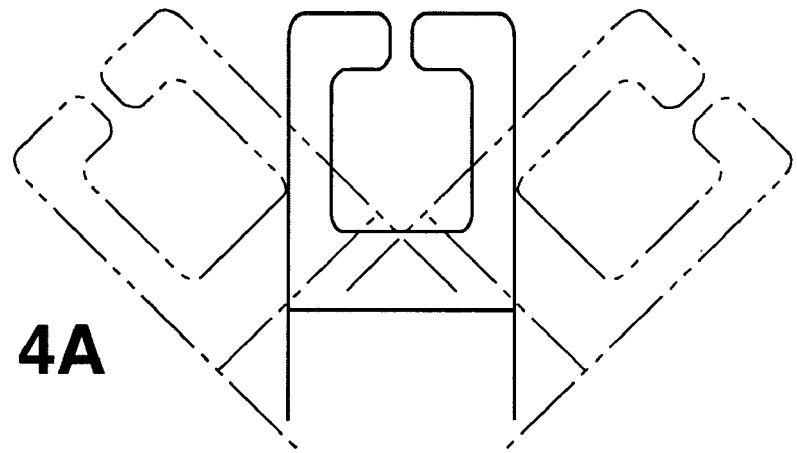
FIGS. 4A and 4B depict alternative exemplary embodiments of a tissue grasping instrument according to the invention.
Figure 4B:
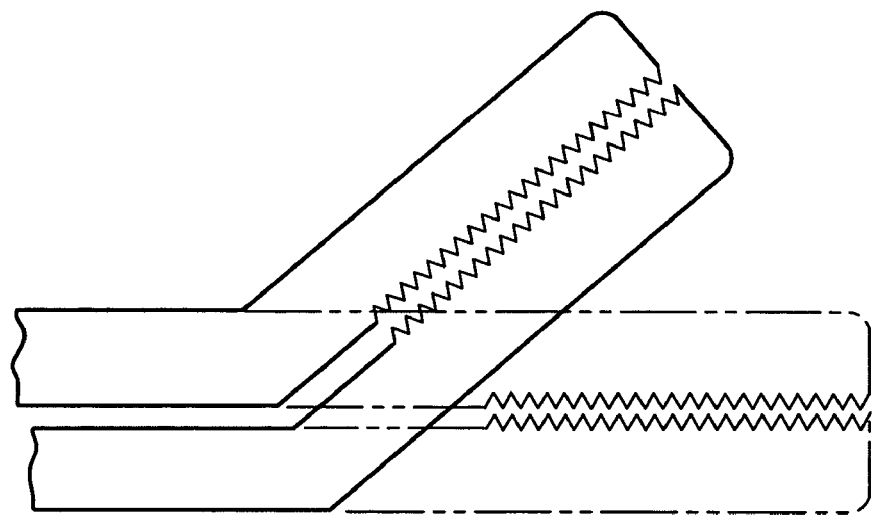

FIGS. 4A and 4B depict alternative exemplary embodiments of a tissue grasping instrument 100 according to the invention. In particular, FIG. 4A shows left and right handed versions of tissue grasping instrument 100, as generally described in U.S. Pat. No. 4,957,498, contents are incorporated by reference herein. It is even possible that jaw portion 40 can be swivelable so one instrument can be used in any orientation. FIG. 4B shows a straight (in-line) jaw portion 40 rather than an angled jaw portion 40.

The above-described instrument is especially suitable for use with the following method.

Figure 5A:
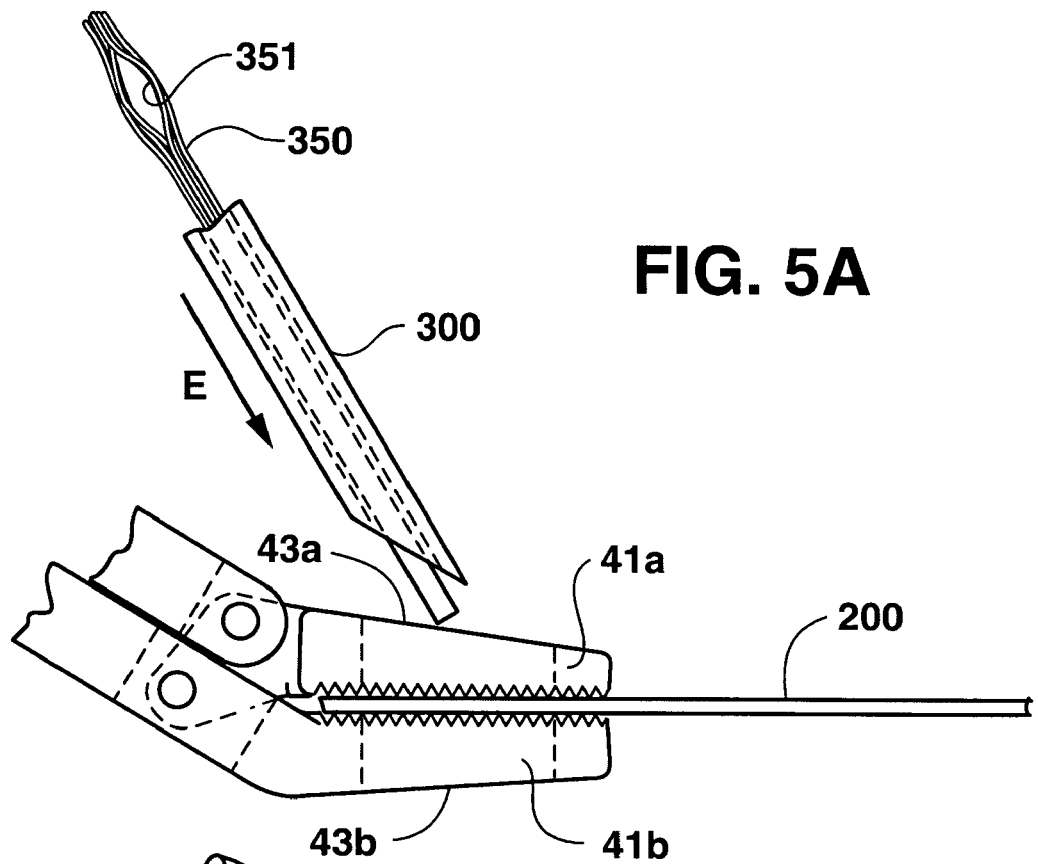
FIGS. 5A, 5B, 5C, 5D, 5E depict the instrument according to an exemplary embodiment used according to an exemplary method according to the invention.

As shown in FIG. 5A, tissue 200 is grasped between first and second jaws 41a, 41b. Feedback from optional spring 9 can tell the doctor if he is squeezing too hard and potentially damaging tissue 200. While tissue 200 may comprise traditional soft tissue such as a patient's existing rotator cuff, the instrument 100 according to the invention is especially suitable for use with tissue 200 comprising a form of acellular tissue matrix, for example, GRAFTJACKET™, as previously mentioned. GRAFTJACKET™ acellular tissue matrix is quite strong and hard to puncture for purposes of suturing;

especially in the closed confines inside of a shoulder during arthroscopy. For purposes of the claims, "tissue" can even mean anything used to symbolize or represent tissue during a demonstration of the instrument according to the invention, e.g., cardboard.

Figure 5B:
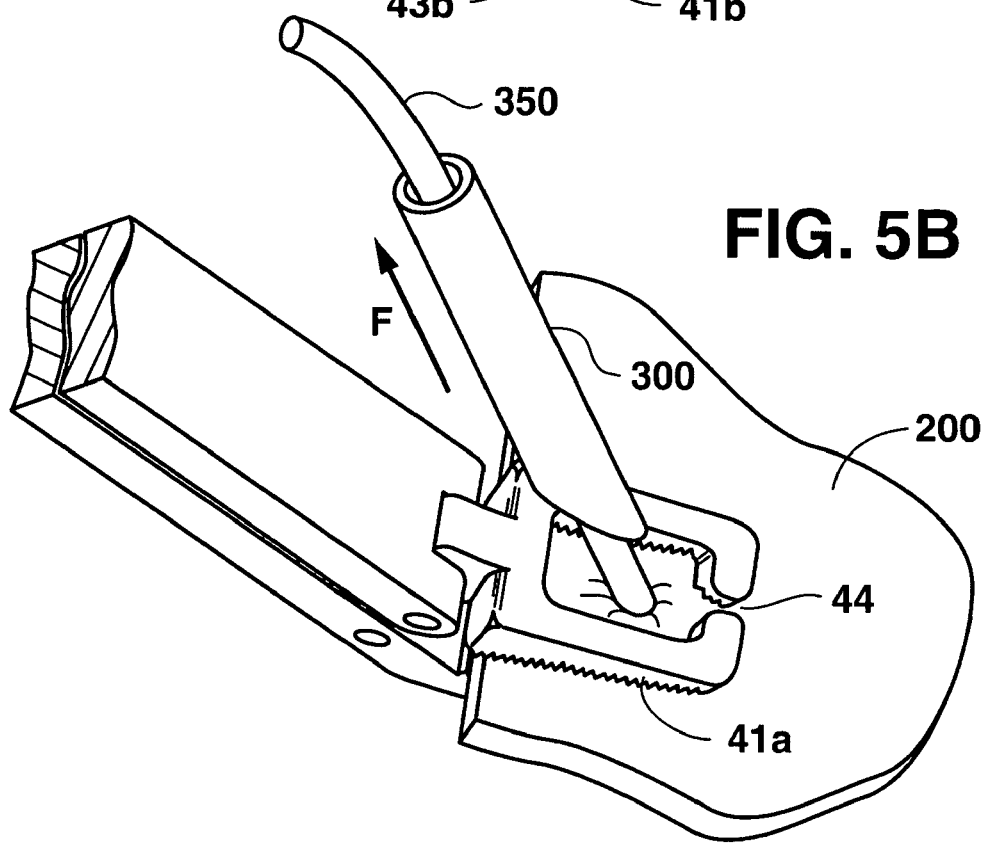
Figure 5C:
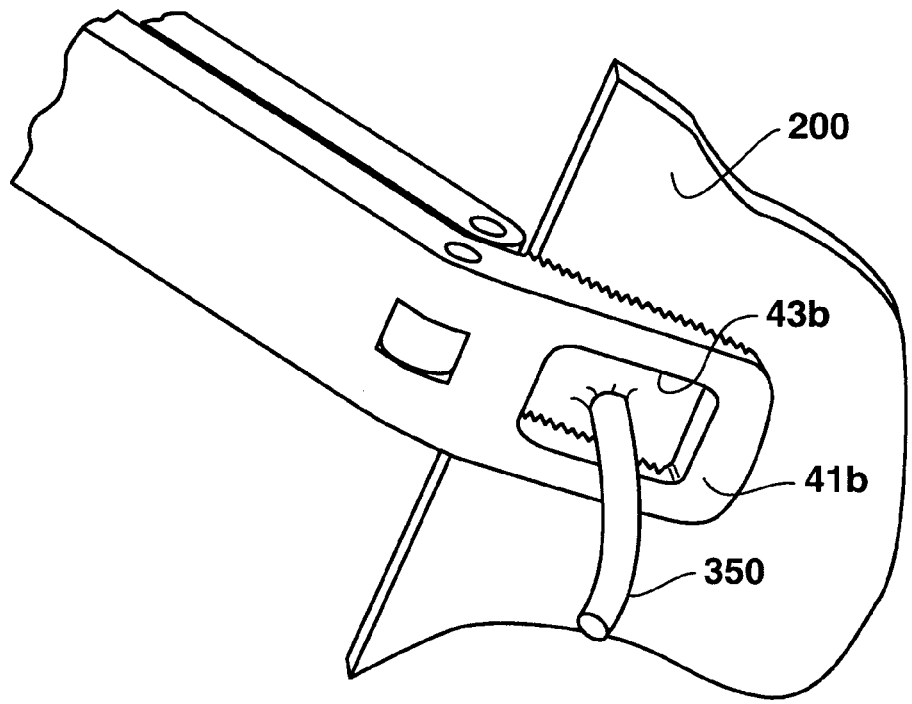
Figure 6:
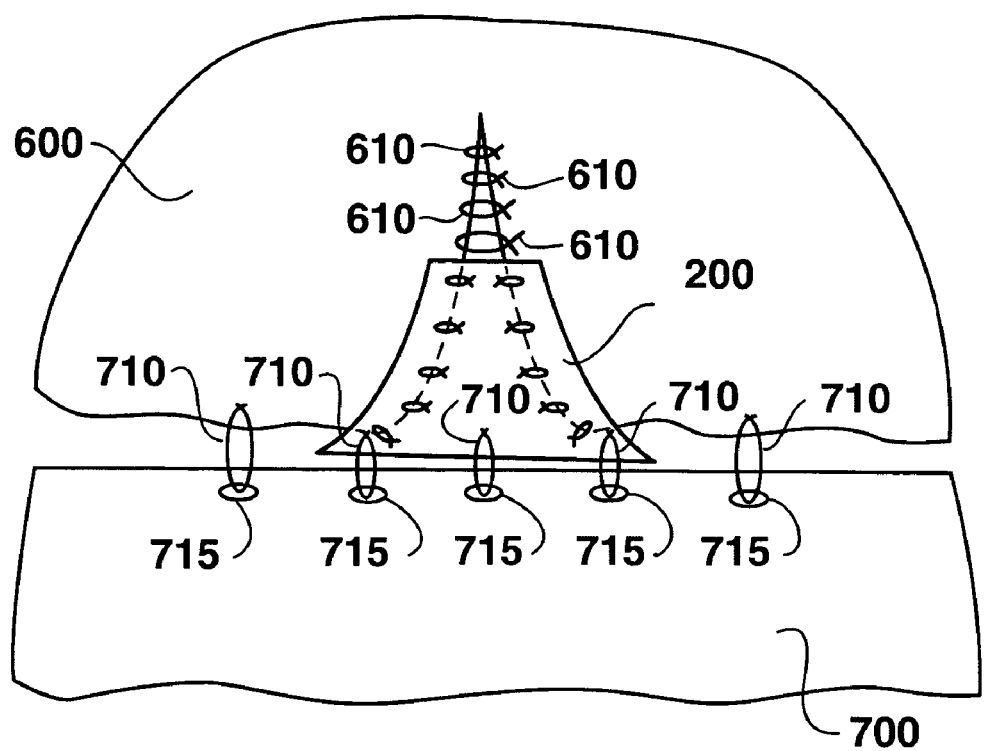
FIG. 6 depicts a tissue graft positioned between bone anchors and a rotator cuff, according to an exemplary embodiment of the method according to the invention.

Hollow needle 300 is moved in the direction of arrow E and used to puncture a hole in tissue 200. This hole will be coincident or align with the center holes 43a, 43b of first and second jaws 41a, 41b, respectively. Shuttle 350, having a conventional suture grasping area 351, is contained/threaded within needle 300. Shuttle 350 gives suture the necessary stiffness to drive it through the various needles and cannulae. While shuttle 350 is conventional, it is possible to have applications in which shuttle 350 is not used. Ultimately, shuttle 350 protrudes through the bottom side of tissue 200 (FIG. 5C). Hollow needle 300 is then removed from the surgical area (FIG. 5B; arrow F). As shown in FIG. 6, this process can be applied occur adjacent already-positioned sutures 710 threaded through suture anchors 715 positioned in the shoulder bone (humerus) 700 or already-positioned sutures 610 located adjacent tear T in the torn rotator cuff 600 of the patient over which the graft 200 is placed for support.

While the preferred method is described with respect to the use of the suture shuttle, a suture with a pre-attached solid needle may also be passed through the openings in the jaws and through the tissue or the graft in a similar manner as the hollow needle with the shuttle/suture combination.

Figure 5D:
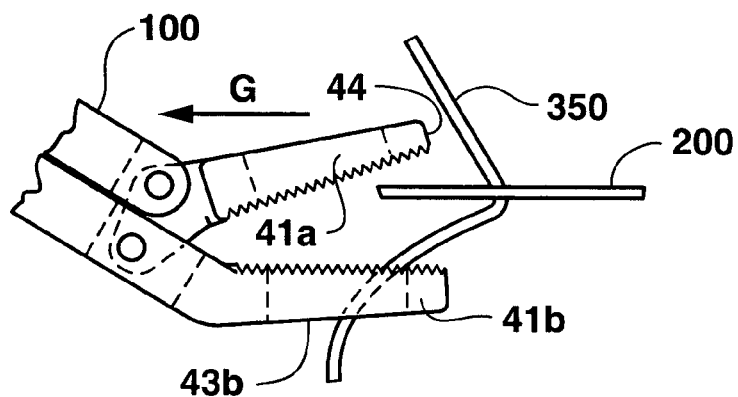

As shown in FIG. 5D, jaws 41a, 41b are then opened (separated). Due to slit 44 of first jaw 41a, the portions of shuttle 350 and suture 360 contained therein are released from the center hole 43a of first jaw 41a and any mechanical influence therefrom. However, on the opposite side of tissue 200, shuttle 350 remains contained (constrained) within the closed perimeter center hole of second jaw 41b (FIG. 5C).

Figure 5E:
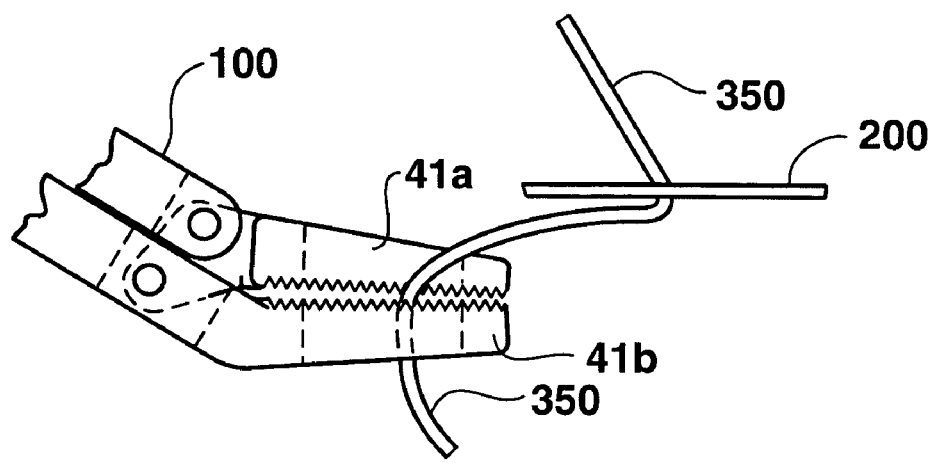

As instrument 100 is moved in direction G (FIG. 5D), away from tissue 200, typically as instrument 100 is being removed from the patient's body, shuttle 350 is pulled by the closed perimeter wall 42b of the center hole 43b of second jaw 41b. Furthermore, as soon as first and second jaws 41a, 41b clear the edge of tissue 200, jaws 41a, 41b can be closed again to grip shuttle 350 to provide additional pulling friction to shuttle 350 and suture 360 (FIG. 5E).

After the leading end of shuttle 350 has been removed from the body/surgical area, suture (not shown) is then threaded in the suture grasping area 351 in a conventional manner and then pulled into the surgical area, also in a conventional manner.

While the invention has been described in the form of a preferred embodiment and method, deviations from the described structure and method are possible while staying within the scope of the invention and the claims.

That which is claimed:

1. A surgical instrument, comprising:
    a support portion, said support portion including a support member and an upper handle, said support member having a narrow elongated configuration, said upper handle extending from a trailing end of said support member in a fixed relationship thereto,
    an actuation member having a narrow elongated configuration, said actuation member slidingly disposed along an upper surface of said support member,
    a lower handle disposed below said support portion, an upper end of said lower handle having a pivot arm, said pivot arm pivotally connected to said support portion adjacent a trailing end of said support member and further pivotally connected to a trailing end of said actuation member,
    an upper jaw having a leading end and a trailing end, said trailing end of said upper jaw pivotally connected to a leading end of said actuation member, a hinge member extending below said trailing end of said upper jaw, and said upper jaw further pivotally connected to a leading end of said support member via said hinge member of said upper jaw,
    a lower jaw, said lower jaw extending from a leading end of said support member and disposed below said upper jaw for use in gripping tissue between said upper and said lower jaws,
    said upper jaw having an upper surface and a lower surface, said upper jaw having a hole passing through said upper surface and said lower surface, said leading end of said upper jaw having a slit formed through a distal end of said upper jaw and extending from the upper surface to the lower surface of said upper jaw and in communication with said hole of said upper jaw, said slit being narrower than said hole of said upper jaw and configured to allow a suture thread in pass therethrough,
    said lower jaw having an upper surface and a lower surface, said lower jaw having a closed perimeter hole extending therethrough between said upper and said lower surface, said closed perimeter hole aligned with said hole of said upper jaw,
    whereby spreading said lower handle away from said upper handle of said support portion draws said actuation member rearward and pivots said upper jaw to an open position, and whereby pulling said lower handle toward said upper handle pushes said actuation member toward a leading end of the instrument and pivots said upper jaw to a closed position adjacent said lower jaw.

2. The instrument of claim 1, wherein said upper and lower jaws have teeth, and wherein said teeth of said upper jaw are out of phase with said teeth of said lower jaw.

3. The instrument of claim 2, where the tips of the teeth of said upper and lower jaws are spaced from each other to thereby prevent damage to a tissue or graft material.

4. The instrument of claim 2, wherein the teeth are coated with a tissue protecting material.

5. The instrument of claim 1, wherein said handle portion contains an overpressure linkage.

6. The instrument of claim 1, further comprising a ratchet arm between said upper handle and said lower handle to thereby prevent twisting of the instrument.

7. The instrument of claim 6, wherein said ratchet is configured for selective locking of said jaws of the tissue grasping instrument at specific incremental positions.

8. The instrument of claim 1, further comprising a spring between said upper handle and said lower handle.

9. The instrument of claim 1, wherein said lower jaw is fixedly attached to said leading end of said support member.

10. The instrument of claim 9, wherein said lower jaw is angled upward from said support member.

11. The instrument of claim 1, wherein said pivot arm of said lower handle is pivotally connected to said lower handle.

12. The instrument of claim 11, wherein said lower handle further comprises a planer spring operatively associated with said pivot connection between said pivot arm and said lower handle, said planer spring configured to give way if too much force is applied to said lower handle, whereupon said lower handle moves with respect to said pivot arm, preventing the application of too much pressure during gripping of a tissue or graft material between said upper and lower jaws.

13. The instrument of claim 1, wherein said lower handle further comprises a safety bias means against applying too much pressure during gripping of a tissue or graft material between said upper and said lower jaws.

14. The instrument of claim 1, wherein said holes of said upper and said lower jaws are coaxial and of the same size.

* * * * *